United States Patent [19]

Steigmeier et al.

[11] Patent Number: 4,526,468

[45] Date of Patent: Jul. 2, 1985

[54] METHOD FOR DETERMINING THE PHASE OF PHASE TRANSFORMABLE LIGHT SCATTERING MATERIAL

[75] Inventors: Edgar F. Steigmeier, Hedingen; Heinrich Auderset, Horgen, both of Switzerland

[73] Assignee: RCA Corporation, Princeton, N.J.

[21] Appl. No.: 509,597

[22] Filed: Jun. 30, 1983

[51] Int. Cl.³ ............................................ G01N 21/01
[52] U.S. Cl. .................................... 356/338; 356/237
[58] Field of Search .............. 356/237, 240, 337, 338, 356/342, 445–448; 250/224, 572, 203 CT

[56] References Cited

U.S. PATENT DOCUMENTS

| 4,314,763 | 2/1982 | Steigmeier et al. | 356/237 |
| 4,352,016 | 9/1982 | Duffy et al. | 250/358.1 |
| 4,352,017 | 9/1982 | Duffy et al. | 250/358.1 |
| 4,391,524 | 7/1983 | Steigmeier et al. | 356/23 |

OTHER PUBLICATIONS

"Light Scattering with Laser Sources," *RCA Engineer*, 15, 82(1970)—Dr. G. Harbeke/Dr. E. F. Steigmeier, (pp. 82–85).

*Primary Examiner*—Bruce Y. Arnold
*Attorney, Agent, or Firm*—Birgit E. Morris; Donald S. Cohen; Joseph D. Lazar

[57] ABSTRACT

A method of determining the crystalline or structural quality of phase transformable material such as silicon uses light scattering. The material is exposed to a beam of light of a selected wavelength. Scattered light having an intensity above a threshold is detected to provide a signal which is used to control the intensity of a display beam of a visual display device. The threshold is varied to thereby vary the display beam intensity so as to provide the minimum intensity of display beam which yields a full display. The value of the thusly adjusted threshold intensity is used as a direct measure of the structural quality of the material.

The light scattering process is used to determine the phase of deposited material.

A layer of silicon material annealed from as-deposited amorphous phase material is easily and quickly distinguished from material as-deposited crystalline phase material and subsequently annealed.

10 Claims, 17 Drawing Figures

TAKEN AT THRESHOLD (I)
SETTING 740

Fig. 4a

TAKEN AT THRESHOLD (I)
SETTING 720

Fig. 4b

TAKEN AT THRESHOLD (I)
SETTING 700

METHOD FOR DETERMINING THE PHASE OF PHASE TRANSFORMABLE LIGHT SCATTERING MATERIAL

This invention is a method for determining the crystallographic phase of light scattering material. More particularly, this invention is directed to crystalline silicon material which has been grown in the amorphous phase with subsequent conversion to a crystalline phase by annealing at high temperatures.

BACKGROUND OF THE INVENTION

Silicon wafers useful in the manufacture of semiconductor devices require close scrutiny to detect defects as soon as possible in the manufacturing process. Several apparatus are known in the art for detecting microscopic defects on the surface or near the surface of such devices. One such apparatus utilizes a laser beam that is scanned over the surface of a wafer and includes means for detecting scattered radiation from the wafer surface. The specular reflection is blocked from the detection device by suitable arrangement of the lenses and spatial filters. If the surface of the wafer has an imperfection such as dirt, hills, scratches and the like, the laser beam will be scattered from the imperfection. There are also scattering processes such as Raman scattering, etc., which occur, but the intensity of the light due to such scattering effects is usually negligible. The scattered light from the wafer is collected from about the main axis of the lens and is focused on a detector. The scattered light is converted to electrical impulses which can be counted or, in the alternative, can be displayed as a bright spot on an oscilloscope or other monitor. See U.S. Pat. No. 4,314,763 issued Feb. 9, 1982 to E. F. Steigmeier et al. entitled "DEFECT DETECTION SYSTEM" for a detailed description of such a scanning apparatus.

The use of such light scattering apparatus for detecting surface and subsurface defects by conventional light scanning techniques does not identify or test for the crystalline quality of the semiconductor material. The quality of such material is related to the purity or perfection of the crystallographic growth of the material on an atomic or microscopic scale. Deviations from the ideal crystallographic perfection can be said to be a reduction in the quality of the material. The better the quality the closer the material is to the ideal crystallographic perfection. The term "crystallographic quality" includes structural conditions known to more or less extent in the art. For example, "mosaic spread" can be a deviation from the ideal crystallographic structure caused by slight misorientation of the crystalline axis directions or mosaic spread can be manifested by larger misorientations of one area of the material against the adjacent area. Such larger misorientations might be called "grain" or "twinning." Other structural deviations of the crystalline structure of a semiconductor material are continuously being identified and analyzed in the art. However defined, the quality of the crystalline structure, it should be understood, is distinguished from the defects on the surface of the semiconductor material in the form of scratches, recesses, particulates, and the like.

In U.S. Pat. Nos. 4,352,016 and 4,352,017, issued Sept. 28, 1982, both entitled A METHOD AND APPARATUS FOR DETERMINING THE QUALITY OF A SEMICONDUCTOR SURFACE, based on the inventions of M. T. Duffy, P. J. Zanzucchi, and J. F. Corboy, Jr., there is described a method and apparatus for determining the quality of the material of a semiconductor surface. In brief, the surface quality of the semiconductor material is determined by exposing the semiconductor surface to two light beams of different wavelengths or wavelength ranges (e.g., ultraviolet at 2,800 angstroms and near ultraviolet at 4,000 angstroms). A portion of each of the respective light beams is reflected from the semiconductor surface. The intensity of each reflected beam is measured to obtain an intensity difference whereby the magnitude of the difference is a measure of the quality of a semiconductor material. While the quality of semiconductor material can be tested or evaluated quite well using the ultraviolet two wavelength technique described in the above-identified Duffy, et al. patents, the time required to make such tests can be very long and not well suited for on-line evaluations needed in modern day semiconductor processing and manufacturing.

SUMMARY OF THE INVENTION

The present invention uses light scattering techniques to provide an indication of the crystallographic phase of phase transformable material. The method comprises exposing the surface of a deposited material of a given crystallographic phase to a wavelength of light sufficient to penetrate the material to a depth of interest, detecting the scattered light, and adjusting the threshold of intensity of the detected scattered light so that the display of the detected signal on a visual display is sufficient to provide a full display of the surface. The value of the threshold adjustment is a direct measurement of the crystallographic phase of the material.

According to another aspect of this invention, a rapid acceptability characterization of phase transformable material can be performed, in order to determinine (a) whether the deposited material is in the amorphous as compared to the crystalline state; or (b) whether the crystalline material had been deposited previous to annealing crystallization in the amorphous as compared to the crystalline state.

DETAILED DESCRIPTION OF PREFERRED EMBODIMENTS

Figure 1:
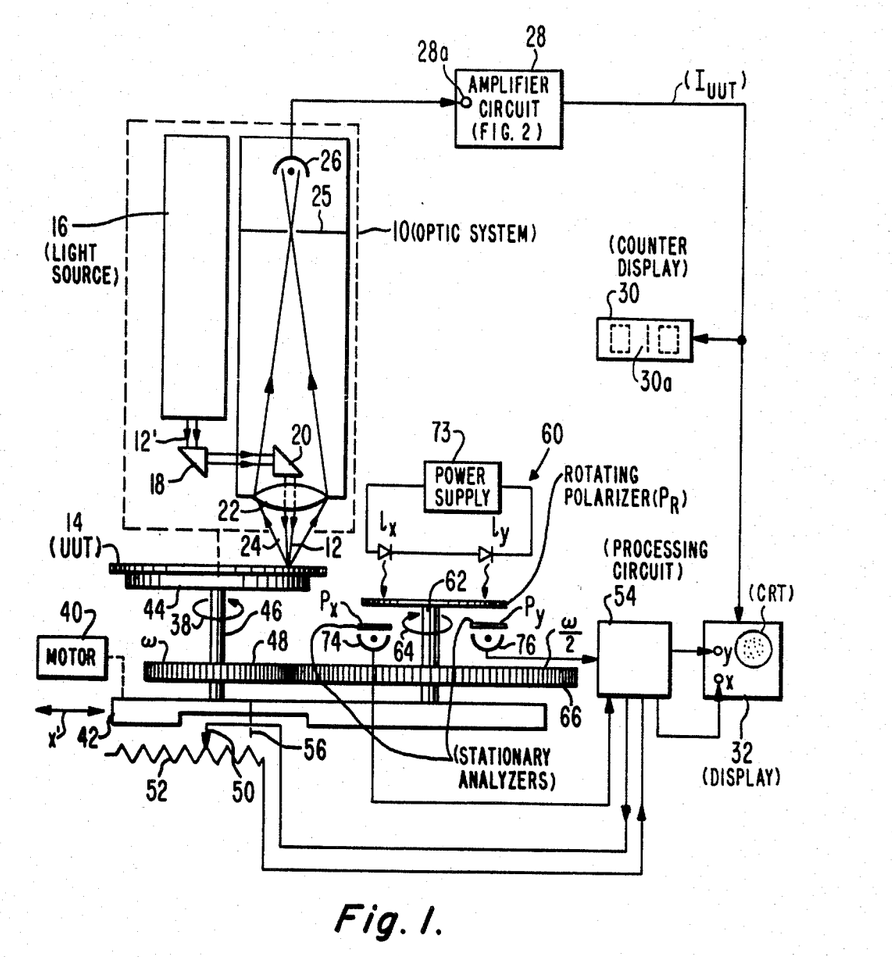
FIG. 1 is a schematic of an optical scanner apparatus useful in practicing the method of the present invention.

Before proceeding to a detailed description of the method for determining according to the present invention the crystallographic phase of semiconductor material, reference is made to FIG. 1 illustrating a suitable optical scanner for which the method of the present invention is used. The apparatus shown in FIG. 1 and described in detail in the above-identified Steigmeier et al. patent, comprises an optical system 10 which includes a light source 16 providing a beam of light 12' passing through a series of prisms 18 and 20 and then through a focusing means such as lens 22 forming beam 12. The light source 16 provides a light of any selected wavelength and includes light in the infrared (IR), visible or ultraviolet (UV) light spectrum. Light source 16 may be a low power laser, for example, a HeNe laser producing light at 6323 angstroms in wavelength which is focused by lens 22 into a spot 250 μm in diameter. For optimized conditions (of minimum beam spot size) elliptical spot sizes of 40 μm by 250 μm may be produced by inserting an appropriate cylindrical/spherical lens system (not shown) in between the two prisms 18 and 20. Beam 12 of the laser light is projected onto the surface 14 of an object such as the unit under test (UUT). The unit under test may be a wafer of silicon as used in the manufacture of integrated circuits (IC) and other semiconductor devices. The UUT, for example, is a wafer of silicon on sapphire (SOS). However, wafers of epitaxial deposited silicon on substrates such as silicon, spinel, etc., may also be used. Moreover, the quality of dielectric material and of amorphous silicon material may also be determined as covered by our above-identified co-pending application Ser. No. 244,060 now U.S. Pat. No. 4,391,524. According to the present invention, the crystallographic phase of phase transformable material is determined as will be explained hereinafter.

The position of the light source 16 is not critical, but the position of the beam 12 between the prism 20 and object surface is important. The axis of the beam is preferably substantially perpendicular to the surface 14. Light generated by laser 16 is preferably scanned over the surface 14 of the UUT and is reflected back through the lens 22 via beam pattern 24 and collected on a photodetector 26 which is positioned along the axis of the beam 12. Lens 22 in combination with prism 20 serves as a first of two spatial filters to specular reflected light along the axis of beam 12. Defects that appear on the surface 14 of UUT may be as small as 1 μm in area. A defect may extend beyond the diameter of the laser beam, namely beyond 250 μm, in which case its shape, as distinguished from its mere size, will be detected by the scanning process. Surface defects scatter a sufficient amount of light beyond prism 20 so as to be detected by photodetector 26. In general, since an ideally optically flat surface will not scatter light, the defect will have surface portions that are not optically flat with respect to the incident light.

Figure 2:
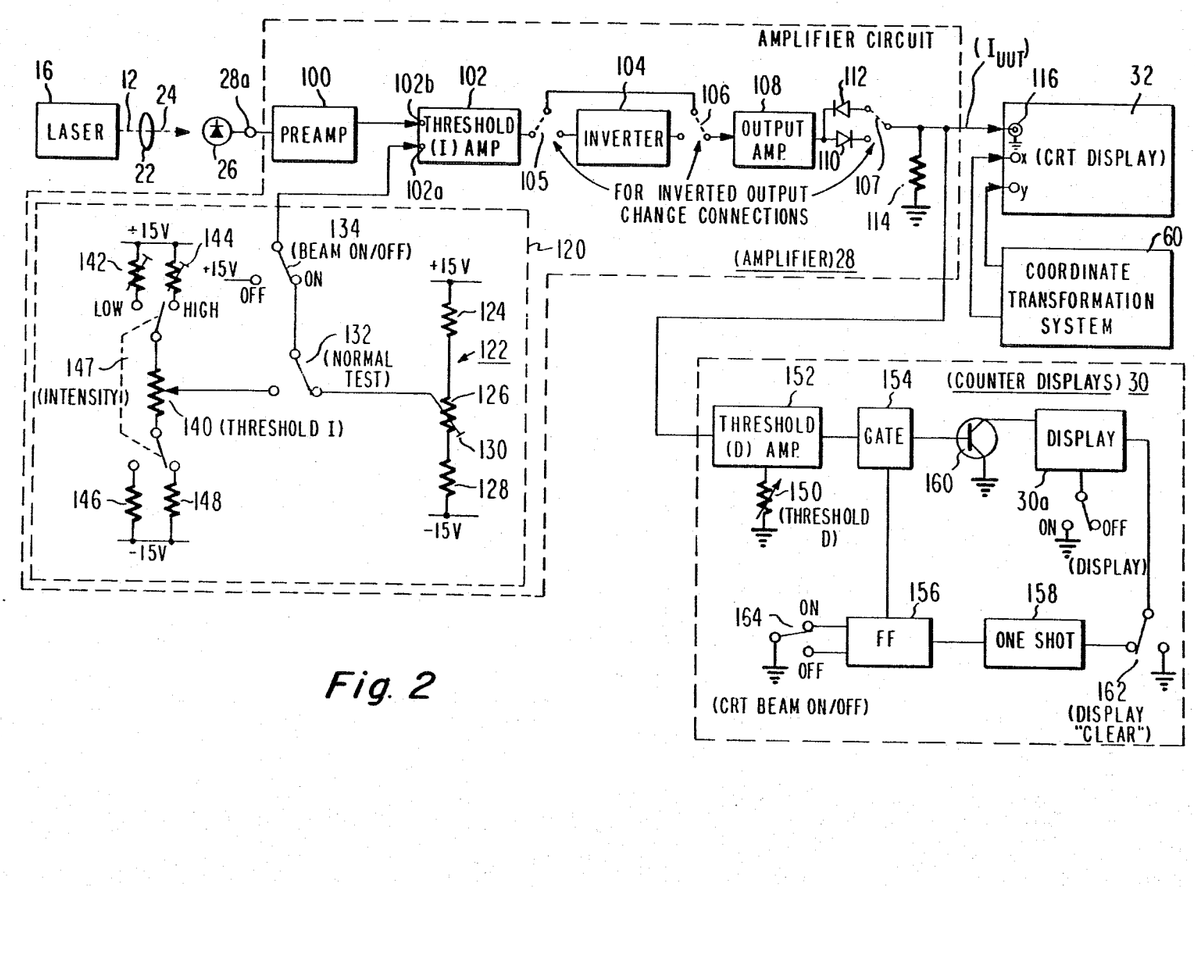
FIG. 2 is a block schematic of the amplifier circuit of the scanner illustrated in FIG. 1.

An aperture mask 25 acts as the second spatial filter in optical system 10 and prevents ambient light from being projected onto the detector 26. The output of detector 26 is applied to an amplifier circuit 28 which provides an output signal to either or both a counter display 30 or a cathode ray tube (CRT) display 32. Counter display 30 counts the number of defects that are detected during a scan of beam 12. The CRT display 32 provides a visual display of the relative spatial distributions of the locations of the defects on the UUT. Amplifier 28 is a high gain amplifier analogue in nature and produces an amplified output of the detector output with respect to the input signal it receives from detector 26 at terminal 28a. This results in gray scale in the CRT display 32, the intensity of the indications of defects on the CRT screen being indicative of the defects. A more detailed schematic of amplifier 28 is shown in FIG. 2 to be described.

In the form of the scanner shown in FIG. 1, the beam 12 scans the UUT in spiral fashion and the electron beam of the display 32 is also scanned in spiral fashion. The UUT may be a circular surface and for such purposes a spiral pattern is useful. For square shaped surfaces a circular inscribed portion is scanned. If desired, the pattern may be converted into an X-Y display which is achieved by the coordinate transformation system 60 which transforms polar coordinates of the beam striking at surface 14 into suitable rectangular coordinates which are applied as X-Y coordinate inputs for the display 32. A detailed description of the polar coordinate system 60 is not given here, but a more detailed description is given of this and other features in the above-identified U.S. Pat. No. 4,314,763, described above and hereby incorporated by reference.

In brief, the coordinate system 60 includes polarizer $P_R$, spaced, stationary analyzers $P_y$ and $P_x$, and detectors 74 and 76 excited by the light emitting photodiodes $L_x$ and $L_y$, which are energized by power supply 73. The system 60 includes a shaft 62 rotating in direction 64 over rotatable table support 42 slidable by motor 40. A gear 66 connected to shaft 62 is meshed with gear 48 so that the polarizer $P_R$ rotates at a predetermined angular speed, typically one half the angular speed of the UUT on table 44, rotated by shaft 46 in direction 38. The light from the diodes $L_x$ and $L_y$ are passed through the polarizer $P_R$ and detected by detector 74 and 76 and applied to the processing circuit 54. A wiper arm 50 is connected (dashed line 56) to the table 42 and moves with the table 42 as the table translates in the direction x'. The wiper arm 50 is part of a potentiometer 52 which is connected to processing circuit 54 provides the X and Y signals for application to the CRT 32 in the manner described in the above-identified U.S. Pat. No. 4,314,763 of Steigmeier et al.

In operation, when the incident beam 12 is positioned at the center of the UUT, the output of amplifier 28 is zero. As the beam 12 is moved from the center, signals are detected by detector 26 and applied to amplifier circuit 28 and applied to display 32. The display is scanned in an X-Y direction, providing a visual display corresponding to the scattered light from the beam 12. The display appears as bright spots and positions of the spots on the display screen correspond to the spatial distribution of the locations of the defects on or close to the surface of the UUT.

Reference is now made to FIG. 2, which shows particularly the amplifier circuit 28 in detail and its relation to other portions of the system. Laser 16 provides a fixed intensity beam 12 which is scattered as beam 24 which, in turn, is detected by detector 26. The output of detector 26 is coupled via terminal 28a to a preamplifier 100 which in turn is coupled to a threshold current amplifier 102 and thence through one way or another single pole, double throw switch or straps 105 and eventually switch 106. The threshold signal from amplifier 102 is either applied directly to an inverter 104 or, in the alternative, to an output amplifier 108. Single pole, double throw switch 107 inserts either one of diodes 110 or 112 in the circuit depending upon the insertion or removal of inverter 104 by switches 105 and 106. Inverter 104 is used, if desired, to invert the output signal of amplifier 102 whereby the display of a detected defect signal will be inverted. Output resistor 114 (connected to ground) provides the output signal which is applied to the cathode of the CRT 32, as at terminal 116.

A threshold control network 120 provides a means for controlling to a predetermined or preselected value the intensity I of the beam of the CRT display 32. The network 120 comprises for testing a reference potentiometer 122 formed of serial resistors 124, 126 and 128 connected between +15 volts and −15 volts. An adjustment tap 130 is connected to one terminal of a single pole, double throw switch 132, the common terminal of which is connected to another switch 134 and thence to the input 102a of "threshold amplifier" 102. This network 120 provides in a test mode an adjustable voltage to the threshold (I) amplifier 102 to provide a suitable test signal for display on the CRT display 32 for alignment amplifier testing purposes, etc. Threshold amplifier 102 is a suitable operational amplifier having a first input 102b and a second input 102a. The network 120 with the switches 132 and 134 in the position as shown provides a control voltage to terminal 102a of amplifier 102 as the test mode of operation during which the laser is scanning the UUT or wafer. In this test mode a light emitting diode 60a is triggered by the coordinate transformation system 60 to flash light pulses four times per revolution of the wafer UUT (14) at the detector 26. The output signal of detector 26 after amplification through preamplifier 100 and amplifier 102 and 108 produces a test pattern on the CRT display 32 for judging the good alignment values of the optics and the good working condition of the electronics.

For normal operation to preset the predetermined threshold at which the CRT beam provides a predetermined intensity I, a threshold intensity adjustment potentiometer 140 is connected by ganged switch 147 between either one of a pair of selectable resistors 142 and 144 connected in common to +15 volts, the other terminals being connected to switch 147 through a pair of resistors 146 and 148 to −15 volts. The resistors can be selected to provide different voltage ranges to thereby change the intensity of the CRT beam over a wide range of values as desired.

In operation, with switches 134 and 132 positioned to the "normal" position opposite to that shown in FIG. 2, the intensity threshold (I) control 140 will be in the circuit. By adjusting potentiometer 140, the intensity (I) of the CRT beam may be adjusted to a predetermined value. Suitable calibration indicia (for example, "0" to "1000" on the potentiometer are provided (not shown) as a repeatable reference of the selected position of the potentiometer 140.

In addition to the threshold (I) intensity control network 120, a second threshold (D) control 150 is provided to modify the intensity signal ($I_{UUT}$) for counting display 30. The D threshold adjustment 150 provides a reference adjustment of a threshold amplifier 152 whose output is coupled to the input of a gate 154 which in turn is triggered by flip-flop 156 which is triggered by one shot 158. Gate 154 is coupled to transistor 160 which in turn is coupled to counter 30a of display 30 shown in FIG. 1. With contact switch 162 normally in the position shown, triggered events will be registered in the display 30 and with the switch 162 operated momentarily to the other position the display 30 is cleared to "0000." Switch 164 is a switch for controlling the CRT beam according to the switch positions as shown. The coordinate transformation system 60, described above for FIG. 1, as shown in block form is coupled to terminals X and Y of the CRT scope display 32 to provide a signal for controlling the X-Y display pattern described above.

Thus, the threshold intensity (I) potentiometer 140 and threshold (D) potentiometer 150 provide an adjustable detection sensitivity control of the scattered light for the CRT 32 display and the counter display 30, respectively. The sensitivity of detection can be further changed by increasing the gain of the preamplifier 100 and the amplifier 108 or by inserting an attenuator (not shown) between the two. The intensity of the CRT display beam is adjusted by the threshold (I) potentiometer 140 to increase the detector signal sufficiently to the level at which the CRT 32 displays the detected signal.

In operation, with a UUT in position on the table 44, the scanner provides a beam 12 which in turn results in a scattered beam 24 which will, after detection, provide a display on CRT 32. Defects that may appear will be counted in the typical prior art procedures on counter display 30 and displayed on the CRT. Thus, in the prior art operation of the scanner apparatus defects on the surface of an object of semiconductor material are detected by scanning the surface and adjusting the potentiometer 140 of the threshold (I) control (FIG. 2) at various values to provide a visual display on the CRT of display 32 or a count of defects on counter display 30 as described in detail in the aforementioned Steigmeier, et al. patent application. The particular size of a defect can be identified by calibrations of setting of the threshold (I) potentiometer 140 and/or threshold (D) potentiometer 150.

Figure 3A:
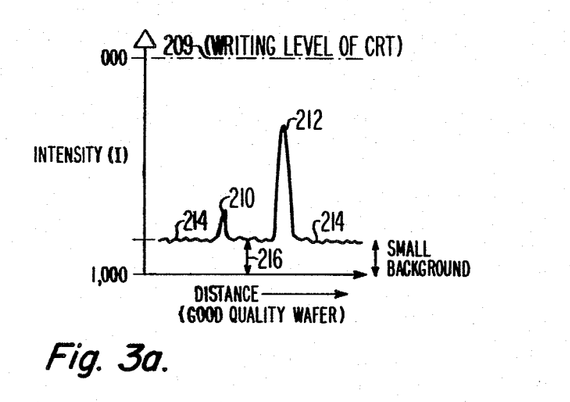
FIGS. 3a and 3b are plots, useful in understanding the invention, of the detector signals of two wafers of different quality.
Figure 3B:
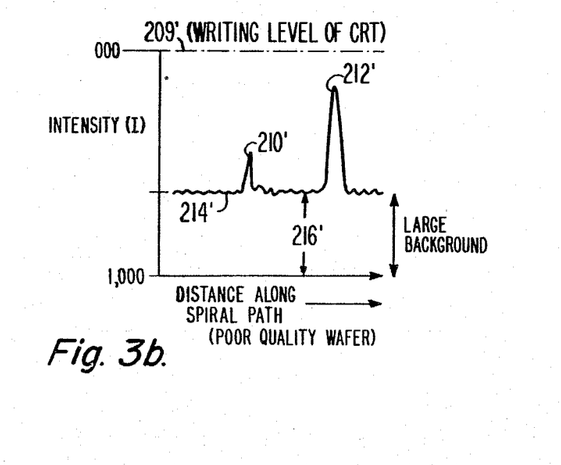

The invention for determining the crystalline quality of the bulk material below the object surface as covered by our copending application Ser. No. 244,060 now U.S. Pat. No. 4,391,524 is based on the discovery that similar identifiable defects of comparable size, appearance, density and the like on each of two different wafers but of different crystalline quality resulted from different adjustments of the threshold (I) potentiometer 140 to get what appeared to be the same defect display. It was discovered after many experiments with this observed phenomenon that a relatively good quality wafer had a significantly different threshold (I) adjustment than a relatively poor quality wafer and that such a parameter adjustment was a repetitive and reliable factor for determining at least the relative quality of the bulk or volume portion of semiconductor material. Reference is made to FIGS. 3a and 3b for a more detailed description of this phenomenon. The intensity (I) of the detected scattered signal is plotted against the distance along the spiral track path of a light scan over the wafer. With the threshold (I) potentiometer 140 set at an arbitrary value of 000 within a range of 0–1000, the display on the CRT display 32 may be represented as illustrated in FIG. 3a. The dotted-dashed lines 209 (FIG. 3a) and 209' (FIG. 3b) represent the preselected full writing level of the CRT. This level can be changed by adjustment of the CRT. The spikes 210 and 212 developed from the background response 214 represent respectively relatively small and large defects (or particulates, such as dust) on the surface of the wafer. The distance 216 represents the relative purity of quality of the bulk portion of the wafer.

Another wafer having similar defects on the surface but having bulk material beneath the surface of poorer quality than the wafer illustrated by FIG. 3a may be scanned at the same arbitrary level of "000" to produce a display such as shown in FIG. 3b. The small and large defects 210' and 212' respectively correspond to the similarly sized defects 210 and 212 illustrated in FIG. 3a. The distance 216' represents the relative quality of the crystallinity of the bulk material of the poorer quality wafer. It is seen that the distance 216' for the wafer of FIG. 3b is significantly greater than the distance 216 for the wafer of FIG. 3a. If for both wafers the threshold I adjustment is now increased from the arbitrary value of "000", the storage scope will produce writing when the background levels 214 and 214' in FIGS. 3a and 3b, respectively, are shifted to the level of lines 209 and 209'. This occurs at the threshold I setting of 710 for the good quality wafer or at the threshold I setting of 660 for the poor quality wafer corresponding to the greater distance between the background 214 and line 209 in FIG. 3a than between background 214' and line 209' in FIG. 3b. Thus, the quality of a wafer such as that illustrated by FIG. 3b writing fully at 660 as compared to the wafer represented by FIG. 3a which is writing fully at 710 can be said to be of poorer quality.

An apparatus of the type described above for providing light scattering from the surfaces of wafers can be used to test or appraise wafers on a very rapid and accurate manner particularly useful for manufacturing of semiconductor material. The invention provides special use for semiconductor material heteroepitaxially grown on substrates such as sapphire, a procedure known in SOS IC processing but may be equally useful for homoepitaxially grown silicon.

The invention of our copending application Ser. No. 244,060, now U.S. Pat. No. 4,391,524 as will now be described in detail by several examples, can be used in both a stationary and scanning mode of the apparatus of the type described in the above identified U.S. Pat. No. 4,314,763 to Steigmeier et al. In the practice of either mode, laser light, having a wavelength preferably in the range of wavelengths between blue and ultraviolet, is impinged on the surface of the wafer under test. The scattered light from the illuminated area is collected as described above and detected and processed. In general, the quality of materials in addition to epitaxial silicon layers for SOS wafers can be determined. For other materials comprising epitaxial silicon layers or silicon thin wafers or bulk wafers, or many amorphous materials, the quality can be determined by having the appropriate penetration depth of the incident light be sufficient to cause the bulk or volume portion of the material to develop scattering. This is done by appropriate selection of the wavelength of light. Moreover, the method may be extended to metal layers or thin films or other light absorbing layers to within the penetration depth of the appropriately chosen light.

Figure 4A:
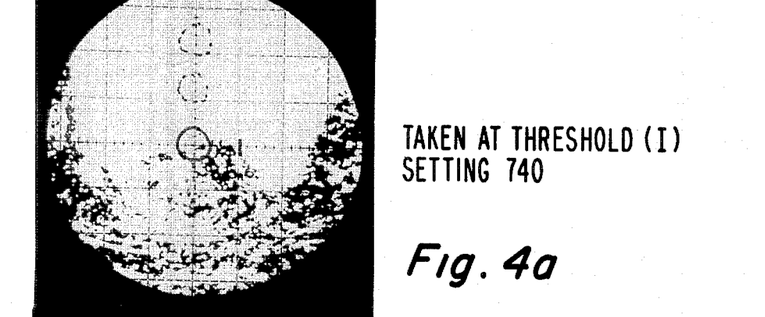
FIGS. 4a, 4b, 4c, respectively, are photographs of the display during the testing of the quality of SOS wafer at different threshold adjustments.
Figure 4B:
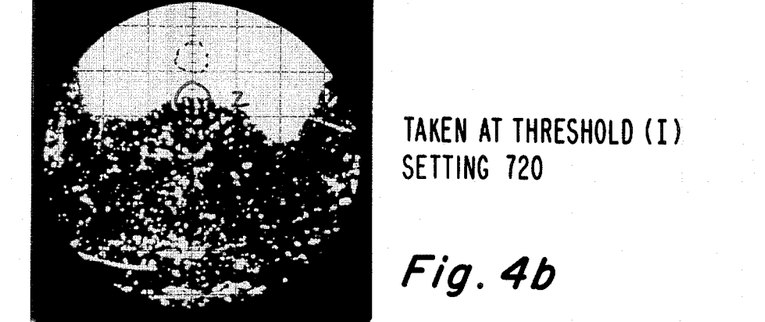
Figure 4C:
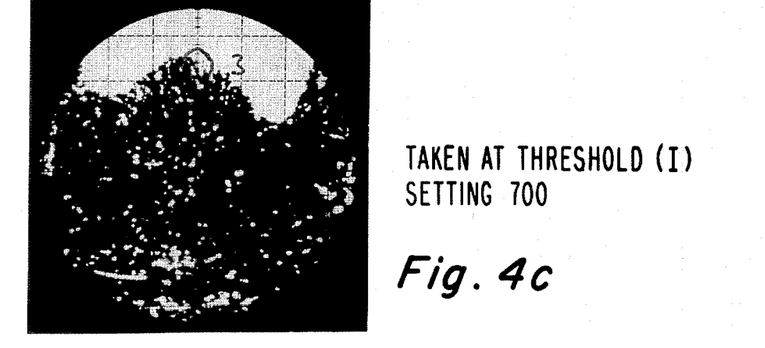

An example of the method of our previous invention covered in application Ser. No. 244,060 is demonstrated by reference to FIGS. 4a, 4b, and 4c. The photographs of FIGS. 4a–4c are that of the CRT of display 32 taken for three different threshold settings of potentiometer 140 for the same SOS wafer in the scanning mode. According to the arrangement of the apparatus, a display that is dark represents relatively good quality material while the white portions of the display represents relatively bad or poor quality material. The wafer display illustrated in FIG. 4a is indicated by a portion "1" represented by a solid circle. Circle 1 is located at the center of the wafer for reference purposes. The two dotted circles aligned vertically above circle 1 represents other surface portions of the wafer, namely, portion 2 and 3 to be discussed with respect to FIGS. 4b and 4c. The wafer as seen in FIG. 4a indicates that the area 1 is at the writing level of the CRT (transition from black to white) for a value of 740 of the threshold I potentiometer setting. Note that the lower half of the wafer is rather close (just slightly better) in quality to portion 1 since it is close to the CRT writing level for the same threshold I setting of 740.

The display illustrated by FIG. 4b was taken when the potentiometer setting is 720. It will be seen that the area portion 2 is at the writing level of the CRT for a value of the threshold I setting of 720. This is indicative of a worse quality of portion 2 than that of portion 1.

FIG. 4c illustrates a display with the threshold potentiometer set at 700. The portion 3 is at the CRT writing level for this (700) threshold I setting. Portion 3 is, therefore, the worst in quality of the three portions 1, 2 and 3 on the wafer.

Thus, the intensity of detected scattered light is a relative parameter depending on the quality of a material. This knowledge is useful in accepting or categorizing wafers to meet certain manufacturing criteria.

Figure 5A:
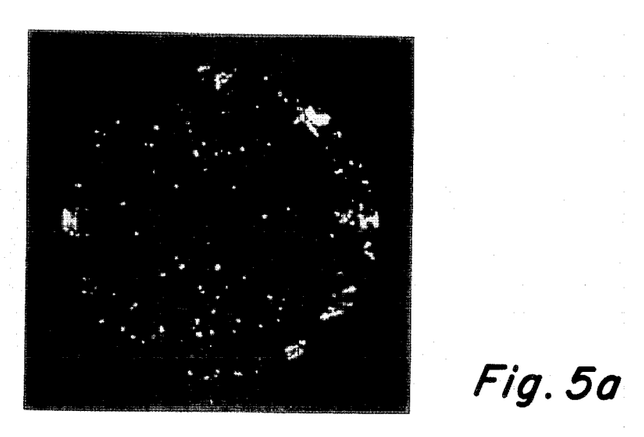
FIGS. 5a and 5b are photographs illustrating the use of the invention to determine a relative good quality and bad quality SOS wafer for production line use.
Figure 5B:
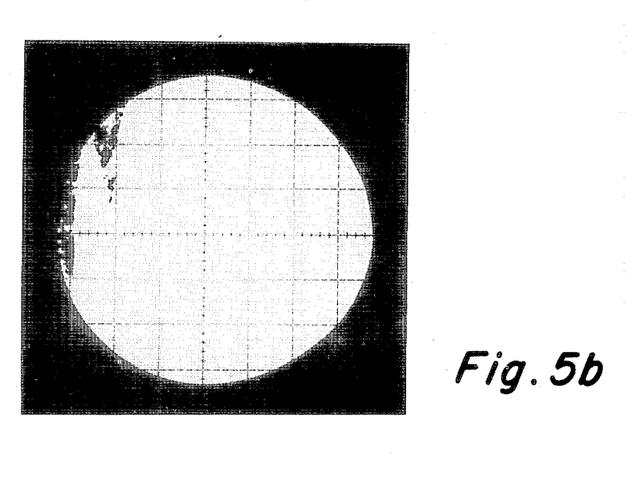

Reference is now made to FIGS. 5a and 5b providing a further illustration of how the scanning method for appraising the quality of semiconductor wafers might be used. The apparatus is set up with a preselected position of the threshold (I) potentiometer 140 set at 710. The value 710 corresponds to a setting that was determined by experiment as being the threshold of acceptability or conversely the threshold of rejection of wafers. An ultraviolet HeCd laser (3,250 angstroms) was used. The quality of many wafers were tested and appraised and found at this setting of I to have been of good quality when the display was substantially dark and poor quality wafers when the display was substantially white. Various surface portions of the wafer could be considered as being within or without a reject criterion. For example, if a wafer was of a poor quality in the peripheral portions and good quality in the central portions, the wafer could be accepted. Other conditions of acceptability can be established according to the criterion set forth by the user. (Compare, for example, FIG. 4a to FIG. 4c.)

FIG. 5a, which is a display of a good quality SOS wafer, is substantially black. FIG. 5b represents a poor quality wafer which provides a display of the scattered light signal that is substantially white. Accordingly, the wafer illustrated in FIG. 5a would be clearly acceptable whereas the wafer described in FIG. 5b would be rejected.

Figure 6:
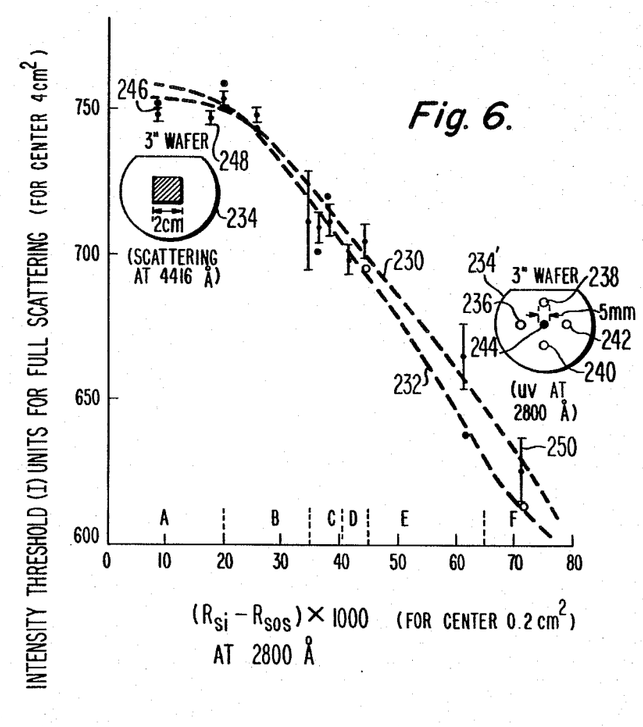
FIG. 6 is a plot showing the correlation between light scattering apparatus and ultraviolet reflection apparatus results.

During the course of tests on many wafers of varying quality, a comparison was made between the results obtained by the ultraviolet reflection techniques described in the above-identified U.S. patents of Duffy et al. and tests made on the light scattering apparatus illustrated in FIGS. 1 and 2, respectively on the same wafers. Reference is made to FIG. 6 which is a plot of a correlation made between the tests of the same wafers by light scattering techniques of our previous invention and the ultraviolet reflection techniques in the above-identified Duffy U.S. patents. The resulting scattering values as represented by the threshold potentiometer 140 settings are indicated on the ordinate of FIG. 6 within the range of 600–750. The abscissa represents the quality of wafers based on the ultraviolet reflection technique as described in the above-identified Duffy et al. patents, determined by the difference of the SOS wafer reflectivity ($R_{SOS}$) from the bulk silicon reflectivity ($R_{Si}$). This difference of the two measurements multiplied by 1,000 provides a relative number (10–80) as plotted along the abscissa. The measurements in this series of tests was done for light at both 4,416 angstroms as represented by curve 230 while a similar set of tests were made with an ultraviolet light laser at 3,250 angstroms represented by curve 232. The wafers tested using the light scattering techniques are illustrated by a typical wafer 234. For these tests the judged portion of the wafer consisted of a square of 2 cm as indicated. The tests for the ultraviolet reflection tests were done on the same wafer as illustrated by wafer 234′. In this instance the UV reflection was made at 5 discrete portions of the wafer represented by portions 236, 238, 240, 242 and 244 of which the portion 244 was selected for the plot of FIG. 6. The UV light was not scanned. The size of the portions exposed to the ultraviolet beam was 5 mm. The vertical bars 246, 248, etc., through 250 represent test data of the maxima, minima and average values of threshold I settings respectively for a particular wafer tested using the light scattering method of the above-identified previous invention, taking into account the variations over the square 234 of the wafer. The plots show very good correlation between the quality of wafers between respective techniques. Arbitrarily, the wafers were grouped as categories A to F as indicated at the lower portion of FIG. 6. The best quality wafers A are seen to include the portion of the curves 230 and 232 that are near or about the threshold setting 750. The poorer quality wafers correspond to category F in which the settings of the threshold adjustments were in the range of 625. Intermediate quality categories B, C, D, and E are clearly seen from the plot.

The previous invention and the present invention, to be described hereinafter, can be practiced in the stationary mode by mainly positioning the beam 12 on the wafer by rotating the table by hand. In practice, the apparatus shown in FIG. 1 would be modified to use a simple table at the place of the UUT on which the wafer can be placed. Alternatively, a simple stage may be provided which is arranged to select five representative locations, such as those illustrated by wafer 234′ in FIG. 6, on which tests could be made successively. This would provide a simpler and faster technique than scanning the entire surface and would provide a simpler technique for making an easier evaluation of the wafer on the selected spots. However, the overall quality of the wafer would be unknown in fact.

While any form of laser light may be used in the practice of the invention (e.g., light within wavelengths of 2,600–5,200 angstroms), it has been discovered that epitaxial layers of SOS wafers are somewhat transparent to blue laser light. As a result, some interference stripes have been observed in the areas that are close to but not at the threshold value of potentiometer 140 to develop a full display of the type described with respect to FIGS. 4a, 4b and 4c. In the preferred form of practicing the invention, an ultraviolet laser light is used. An ultraviolet laser light has been discovered to virtually eliminate the undesirable stripes found in the use of blue laser light.

According to the present invention, in addition to determining the structural quality of a crystalline or an amorphous material, as described hereinabove, a rapid acceptability characterization can be performed of phase transformable material, i.e. of a material which, in a certain process, can be deposited in either the amorphous phase or the crystalline crystallographic phase. Depending on the deposition conditions, either one of the two phases can be used. Thus, this invention can be used to detemine whether the material under test, as-deposited, is amorphous or crystalline. Moreover, the invention can be used to determine whether the film or layer of subsequently annealed (and thus crystallized) material resulted from an as-deposited amorphous layer or from an as-deposited crystalline layer. This feature can be very important, because a film or layer from an as-deposited amorphous layer is of much superior quality in terms of device performance. Examples of these materials will now be described.

Figure 13:
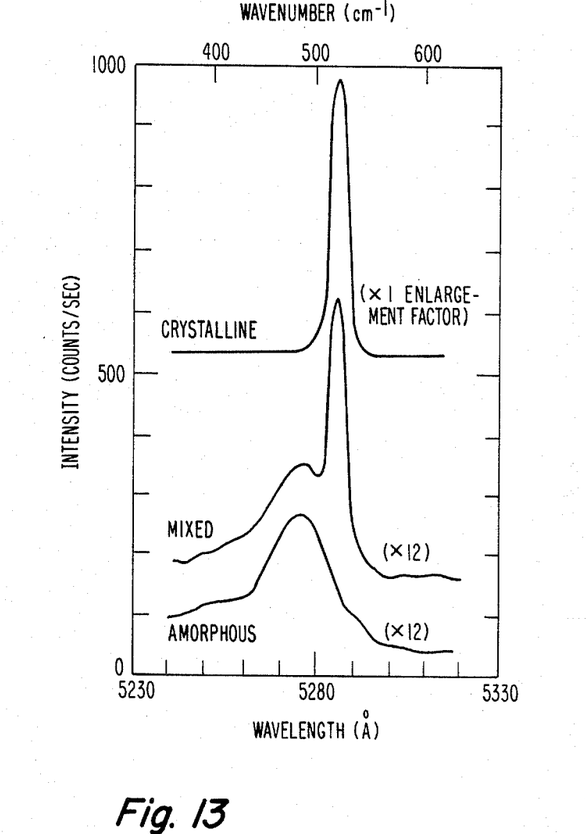
FIG. 13 is a plot of Raman scattering peak intensity against wavelength in angstroms (Å) or wavenumber for films of amorphous, crystalline and mixed material form, the three curves being offset for clarity purposes.

The term amorphous material or amorphous semiconductor material, shall mean, in the present description, material that is without crystallinity as detected by Raman light scattering. We say that a silicon film will have crystalline character if we can detect a Raman spectrum exhibiting a narrow line at about 522 cm$^{-1}$ which corresponds to the optical lattice vibration of silicon. We say that a silicon film is fully amorphous if the Raman line at 522 cm$^{-1}$ is missing, and instead a broad Raman line is observed peaking at about 490 cm$^{-1}$ which usually is much weaker than the crystalline line. We say that a silicon film has partial amorphous and partial crystalline character if both of these features are present in the Raman spectrum at the same time. We shall refer to such film as "mixed." FIG. 13 illustrates the Raman spectrum for the measurements of these materials.

In U.S. patent application, Ser. No. 441,371, filed Nov. 13, 1982 by A. E. Widmer et al., incorporated herein by reference, there is described the use of low pressure chemical vapor deposition (LPCVD) for developing polysilicon layers grown in the amorphous state. This is accomplished by a growth of amorphous silicon at a deposition temperature of 580° C. or less. It has been determined that polysilicon layers annealed from such amorphous depositions are of superior quality for device applications than that which is obtained in more conventional processes in which the polysilicon is deposited at temperatures of 620° C. or greater. Specifically, the amorphous-grown layers exhibit low surface roughness, low internal strain, high structural perfection and other desirable properties after they have been exposed thereafter to annealing temperatures of 850° C. to 1050° C. in the conventional processing steps. Various known techniques are used to characterize the layers in the as-grown state as, for example, by Raman scattering as will be explained hereinafter in relation to FIG. 7. It is desirable in the art to test or characterize such films or layers rapidly. According to the present invention, elastic light scattering measurements using the laser scanner apparatus (FIGS. 1 and 2) can be used to provide a very rapid characterization of such material. For example, a measurement can be made in seven seconds as compared to 7-10 minutes if done with a Raman spectrometer.

The present invention makes use of several important features which are illustrated in FIGS. 7 through 12.

Figure 7:
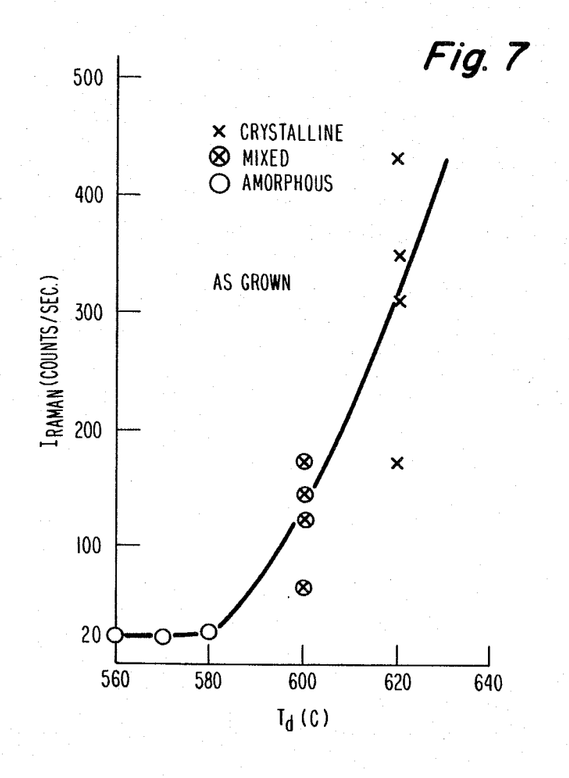
FIG. 7 is a plot of the Raman scattering peak intensity versus temperature of deposition ($T_D$) for various deposited silicon samples.

In a given silicon deposition process, such as LPCVD, described in the Widmer, et al. patent application, it has been shown that one can produce very reproducibly a deposited layer of one or the other crytallographic phase, i.e., an amorphous layer or a crystalline layer, by simply varying the deposition temperature as shown in FIG. 7.

Figure 8:
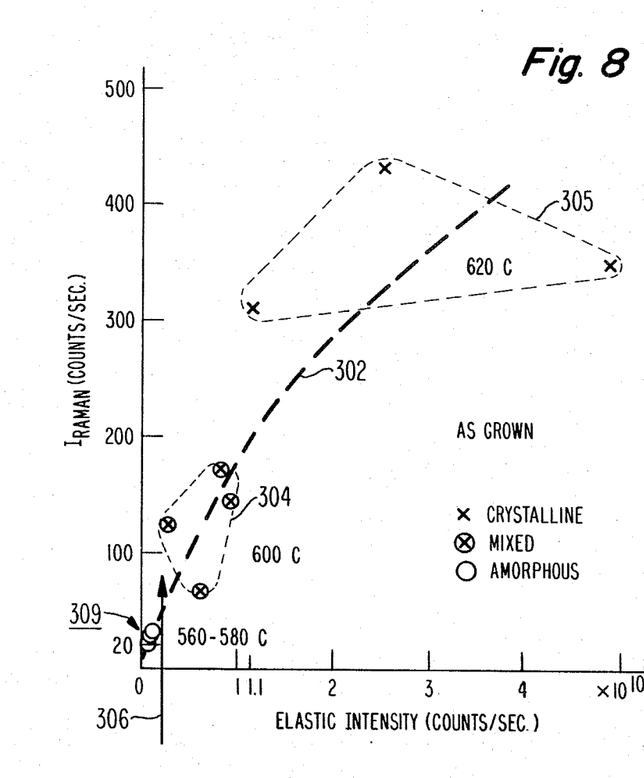
FIG. 8 is a correlation plot of the Raman scattering peak intensity and elastic intensity for various deposited samples of silicon.
Figure 9:
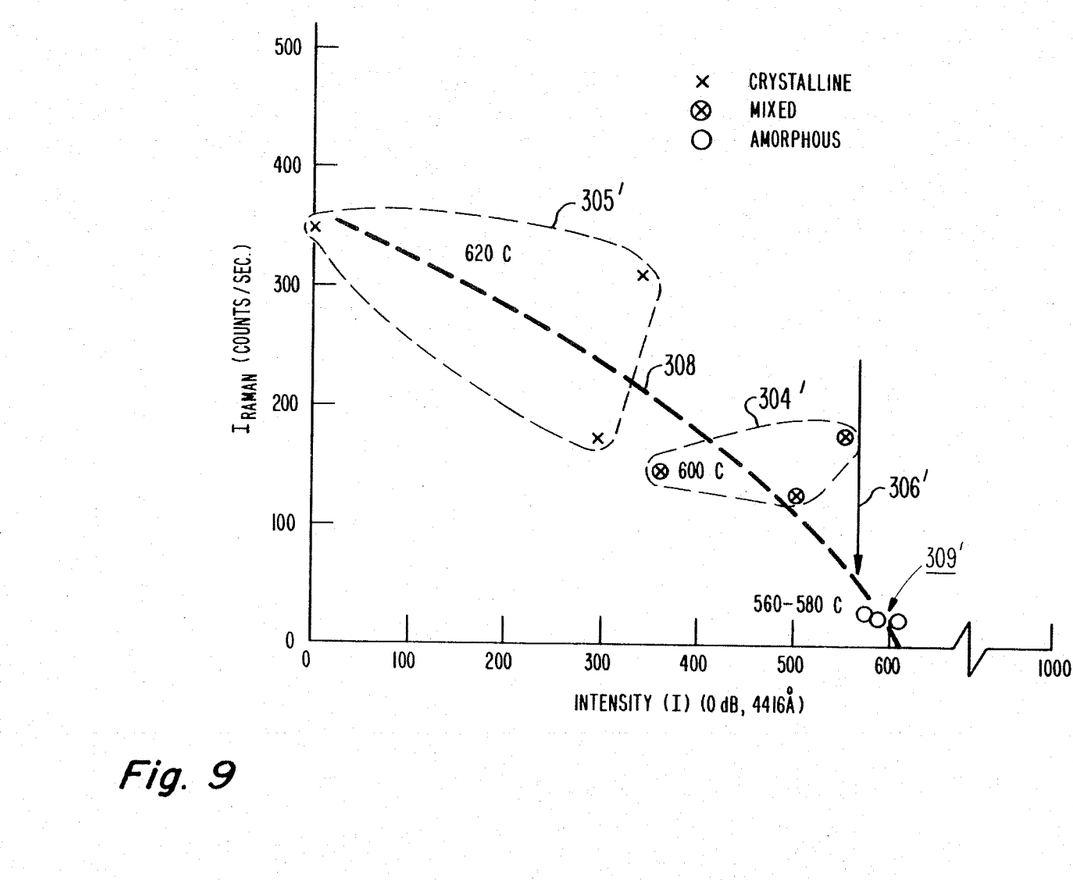
FIG. 9 is a plot correlating Raman scattering peak intensity and the laser scanning units (I) of the present invention.

FIG. 7 is a plot of the Raman scattering peak intensity versus the deposition temperature. A suitable Raman spectrometer for measuring the data shown in FIG. 7, as well as FIGS. 8 and 9, is described in the RCA Engineer 15, 82, (1970) in an article on "Light Scattering with Laser Sources" by G. Harbeke and E. F. Steigmeier. The points plotted in FIG. 7 as a circle represent amorphous material deposited at temperatures within the range of 560° to 580° C. Points x are polycrystalline silicon layers deposited at about 620° C. whereas the points of an x in a circle are polysilicon materials mixed with amorphous materials deposited at about 600° C. It is seen from FIG. 7 that the amorphous silicon layers indicate Raman counts which have an intensity of 20 counts per second for this embodiment.

In addition, FIG. 8 shows that the structural perfection or quality of the as-deposited films, as determined by the inelastic light scattering intensity ($I_{Raman}$), covers a very well defined range for each of the two phases, with good reproducibility, for the above LPCVD process. It is noticed in FIG. 8 that the two well defined ranges of structural quality for as-deposited amorphous and as-deposited crystalline layers, respectively, are distinctly separated, i.e. below $0.2 \times 10^{10}$ counts/sec on the elastic intensity axis for the amorphous layers region (309), and above $1.1 \times 10^{10}$ counts/sec for the crystalline layers (305). In fact, a correlating line 302 can be drawn, as shown, connecting the two regions and passing through the cross-over region ("mixed") 304. Line 306 with the arrow indicates where the phase change at which the amorphous material becomes crystalline.

If the laser scanner (FIGS. 1 and 2) is used for assessing the structural perfection of the as-deposited layers, FIG. 9 shows that the two well-defined regions for the amorphous phase and the crystalline phase are denoted by 309' and 305', respectively, with the connecting line 308 passing through the cross-over region 304'. Line 306' indicates where the phase change occurs.

Figure 10:
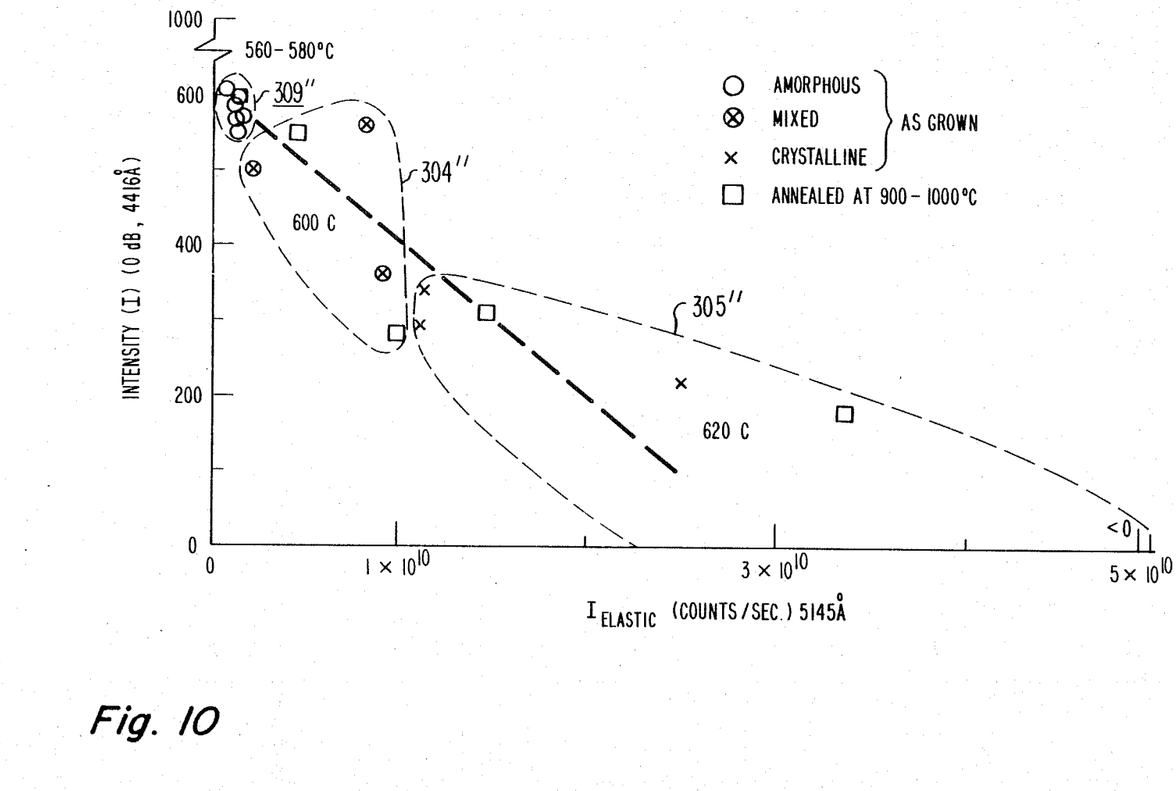
FIG. 10 is a plot correlating the laser scanner units (I) of the present invention and the elastic light scattering intensity.

FIG. 10 shows that the two quantities plotted on the horizontal axes of FIGS. 8 and 9, i.e., the elastic scattering intensity and the laser scanner units (Intensity I), respectively, are, indeed, cross-correlated, and the well-defined region for as-deposited amorphous layers is denoted by area 309", the one for the as-deposited crystalline layers by 305". Based on these data, we have therefore shown, that one can use the relatively slower elastic scattering intensity measurement or even better, the very rapid scanner characterization of the present invention for determining whether an as-deposited LPCVD silicon layer has been deposited in the highly desirable amorphous phase as opposed to the undesirable crystalline phase.

Figure 11:
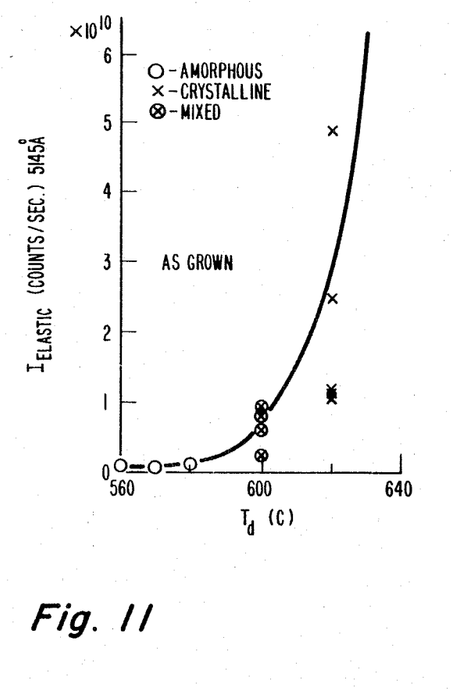
FIG. 11 is a plot of temperature of deposition of various samples of silicon against the elastic light scattering intensity.
Figure 12:
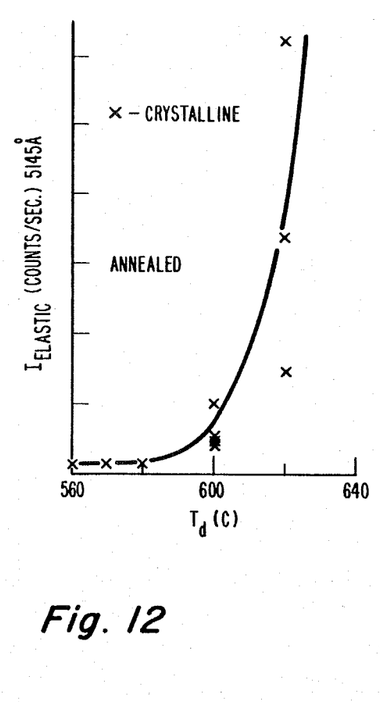
FIG. 12 is a plot similar to FIG. 11 of as-deposited silicon samples that were subsequently annealed.

Reference is now made to FIGS. 11 and 12. It is known in the art that as amorphous material is heated above its deposition temperature it becomes gradually more crystalline, as described in the above-identified patent application of Widmer et al. In particular, it is known, that LPCVD silicon deposited below 580° C. in the amorphous form, is converted to fully crystalline after annealing for 30 min. at 900° to 1000° C., where the given annealing temperatures and time represent convenient integrated circuit process temperatures and time.

FIG. 11 shows the elastic scattering intensity versus deposition temperature of as-deposited layers. Based on what is presented in FIG. 10, the same information as given in FIG. 11 could also be obtained by using the very much more rapid laser scanner characterization, according to the present invention. After the annealing treatment, as mentioned above, FIG. 12 shows the elastic light scattering intensity versus original deposition temperature of the now crystallined layers. Moreover, based on the correlation data of FIG. 10, the same information could as well be obtained by using the much more rapid laser scanner characterization of the present invention. Note that the layers that have undergone annealing treatment are denoted in FIG. 10 by square symbols. The important point to be noted in comparing FIG. 12 with FIG. 11 is that the elastic scattering intensity of the originally amorphous layers is practically unchanged by the annealing treatment. In other words, the very desirable, originally amorphous deposited layers can still be separated from the undesirable, originally crystalline deposited layers after the annealing treatment based on the very much lower elastic light scattering intensity of the former. Alternatively, if the correlation given in FIG. 10 is used, the separation is seen by the much higher laser scanner units (Intensity I) of the former (area 309" in FIG. 10, square symbols) as compared to the latter (area 306" in FIG. 10, shown for simplicity also as square symbols).

In practicing the present invention for rapid acceptability characterization of light scattering material, which can be deposited in a given process, in one or another crystallographic phase, the apparatus (FIGS. 1 and 2) is adjusted for Intensity I for achieving full (blossom) display as described hereinabove. For the LPCVD silicon process, a film of as-deposited amorphous will provide scattering whereby the Intensity I (FIG. 3a) will be large, for example 550 or more scanner units (FIG. 10). If the film is as-deposited crystalline, however, the Intensity I will be much lower, for example, 350 or less scanner units (FIG. 10). Moreover, to distinguish a post-crystallized film which has undergone annealing treatment necessary for device application, the same method can be applied. Thus, the film which originally (as-deposited) has been amorphous exhibits scattering after annealing, whereby the Intensity I (FIG. 3a) will be large, for example, 550 scanner units or more (FIG. 10). Conversely a film which originally (as-deposited) had been crystalline, will exhibit scattering after annealing, whereby the Intensity I (FIG. 3a) will be much smaller than for the former, for example, 350 scanner units or less. The peaks in FIGS. 3a and 3b representing individual defects or dust as described with respect to the previous invention are not relevant, it should be understood, for the present invention.

Thus, the method of the present invention can be used for a rapid and unambiguous acceptability characterization of the highly desirable as-deposited amorphous LPCVD layers whether in the as-deposited or in the post-crystallized (annealed) state. In a typical use of the invention, in practice, one can therefore determine whether a layer intended to be amorphous is or was indeed amorphous, by the process of the invention described hereinabove.

While the invention has been described in terms of evaluating or characterizing silicon material, the invention can be used in other fields where the material is in phase transformable form. For example, in the field of optical discs for information storage, certain materials used in the optical disc are subject to transformation between the amorphous and crystalline state, in response to heat by a laser or other heat source. The materials used for such reversible or phase transformable optical discs comprise the class of tellurium, selenium, frequently called chalcogenides, and binary or ternary alloys thereof with some admixtures. Frequently one refers to the amorphous state of such materials as the "glassy state." This group of materials can be evaluated in the same manner as described by FIGS. 7 through 12. Based on our practice with tellurium and antimony selenides it appears very likely that the invention will find application for this general class of materials and the general field of optical storage discs.

It should be appreciated, according to the present invention, that one can, for a given deposition process and after previous correlation by other methods, determine the crystallographic phase of the material whether it is amorphous, or crystalline, or whether it had been deposited amorphous previous to crystallization. Moreover, these determinations can be achieved very rapidly, for example, within 5 to 10 seconds. In the prior art, the conventional methods for determining such states takes minutes, if not hours, to accomplish. In the field of processing semiconductor material, the invention thus allows for a very rapid determination and characterization of semiconductor materials as they are processed.

What is claimed is:

1. A method for determining the phase of a deposited material having a property of absorbing light to a given penetration depth, said material being capable of being deposited in either of two predetermined phases, comprising the steps of:
    (a) depositing one of said two phases of said material on a surface;
    (b) exposing one or more regions of said material to a beam of light of a selected wavelength;
    (c) detecting light having an intensity greater than a threshold intensity scattered from the exposed material to provide an electrical signal proportional to the intensity of scattered light detected above said threshold intensity;
    (d) applying the electrical signal to a visual display device to control the intensity of the display beam of the device; and
    (e) varying said threshold intensity to thereby vary the intensity of the display beam so as to provide the minimum intensity of display beam which yields a full display of the exposed material, wherein the value of the threshold intensity is a direct measure of the phase in which said material was deposited.

2. The method of claim 1 comprising depositing said material at a first relatively low temperature, and, following said depositing step, annealing said material at a relatively high temperature, whereby the phase of said material as-deposited prior to annealing is determined by said value of intensity.

3. The method of claim 1 comprising depositing said material by low pressure chemical vapor deposition (LPCVD) of silicon in either an amorphous phase at 560° to 580° C. or crystalline phase at 600° to 620° C.

4. The method of claim 1 comprising depositing said material selected from the group consisting of chalcogenides and alloys of tellurium and selenium.

5. The method of claim 1 comprising depositing said material from the chalcogenides group consisting essentially of tellurium and selenium and binary or ternary alloys thereof.

6. The method of claim 1, wherein the light exposing step comprises scanning the light beam of a selected surface portion of the material.

7. The method of claim 1, wherein the light exposing step comprises exposing the material to a plurality of selected spatially separated beams incident on the surface of the material.

8. The method of claim 1, wherein the wavelength of said light is selected from a wavelength within the range of 2,600–5,200 angstroms.

9. The method of claim 1 comprising depositing said material as a layer of amorphous silicon on a layer of single crystal silicon.

10. The method of claim 1 comprising depositing said material as a layer of polycrystalline silicon on a layer of single crystal silicon and annealing said polycrystalline layer prior to steps (b) to (e).

* * * * *